United States Patent
Dauner

(10) Patent No.: US 8,734,731 B2
(45) Date of Patent: May 27, 2014

(54) APPARATUS AND METHOD FOR FRACTIONATING LIQUIDS CHARGED WITH PARTICLES

(75) Inventor: Michael Dauner, Nehren (DE)

(73) Assignee: Rapid Samplins Technologies, AG (DE)

( * ) Notice: Subject to any disclaimer, the term of this patent is extended or adjusted under 35 U.S.C. 154(b) by 1231 days.

(21) Appl. No.: 12/083,288

(22) PCT Filed: Oct. 26, 2006

(86) PCT No.: PCT/DE2006/001898
§ 371 (c)(1),
(2), (4) Date: Oct. 6, 2008

(87) PCT Pub. No.: WO2007/048400
PCT Pub. Date: May 3, 2007

(65) Prior Publication Data
US 2009/0236291 A1    Sep. 24, 2009

(30) Foreign Application Priority Data
Oct. 26, 2005 (DE) .......................... 10 2005 051 645

(51) Int. Cl.
*B01D 21/24* (2006.01)
*B01D 21/30* (2006.01)
*B01D 21/34* (2006.01)

(52) U.S. Cl.
USPC .............. 422/500; 422/50; 210/739; 210/147

(58) Field of Classification Search
USPC ..................... 422/101, 500, 50; 210/739, 147
See application file for complete search history.

(56) References Cited

U.S. PATENT DOCUMENTS

| 4,103,722 A | 8/1978 | Zollinger |
| 5,108,704 A | 4/1992 | Bowers et al. |
| 5,208,160 A * | 5/1993 | Kikyotani et al. ............ 435/270 |
| 5,595,653 A | 1/1997 | Good et al. |
| 5,670,054 A * | 9/1997 | Kibbey et al. ................. 210/656 |
| 6,020,186 A * | 2/2000 | Henco et al. ................ 435/287.2 |
| 6,082,417 A * | 7/2000 | Horn ............................. 141/130 |
| 6,136,555 A | 10/2000 | Jones |
| 6,197,198 B1 * | 3/2001 | Messinger et al. ............ 210/656 |
| 2006/0027490 A1 * | 2/2006 | DeMarco ................... 210/198.2 |

FOREIGN PATENT DOCUMENTS

| DE | 27 37 589 | 3/1978 |
| DE | 694 08 461 | 8/1998 |
| DE | 198 17 081 | 10/1999 |
| DE | 102 01 858 | 8/2003 |
| EP | 1 588 765 | 10/2005 |
| GB | 713535 | 8/1954 |

OTHER PUBLICATIONS

Belarbi, E.H.; Molina, E.; Christi, Y.; "A process for high yield and scaleable recovery of high purity eicosapentaenoic acid esters from microalgae and fish oil," 2000, Enzyme and Microbial Technology, 26, pp. 516-529.*

* cited by examiner

*Primary Examiner* — Christine T Mui
(74) *Attorney, Agent, or Firm* — Vance Intellectual Proerty, PC

(57) ABSTRACT

Provided is a device and a method for fractionating particle-containing liquids. The device comprises at least one separation apparatus and at least one collection apparatus. The collection apparatus has at least two containers and the outlet of the at least one separation apparatus opens into a distribution system that has a repositionable outlet that can be oriented selectively toward the input opening of the containers. The distribution system adds the liquid to the at least two containers of the collection device in a controlled manner as a function of event or time.

26 Claims, 3 Drawing Sheets

APPARATUS AND METHOD FOR FRACTIONATING LIQUIDS CHARGED WITH PARTICLES

This Application is a national stage filing of and claims the benefit of PCT/DE2006/001898.

BACKGROUND OF THE INVENTION

The invention proceeds from a device and a method for fractionating particulate-containing liquids, for instance chemical or biological solutions, particle suspensions, emulsions, among others, in which is or are disposed one or a plurality ingredients that are to be determined and/or investigated.

For determining and/or investigating ingredients that are disposed in particulate-containing liquids, for instance for analyzing a metabolic profile, the ingredients must be separated out of the liquid. This generally occurs using mechanical processes such as precipitation, filters, and centrifugation, or using mechanical means by extraction. The undesired particulates, for instance components of a nutrient medium in which biological units such as phages, cells, tissue, organs, organisms, or parts thereof, inter alia, were cultivated, or from a decomposition process of such components based on biological units, such as cellular debris, inter alia, are retained by the aforesaid methods, while the liquid with the ingredients to be determined or investigated are captured in separate containers (DE 102 01 858 A1) or drawn out of the apparatus (DE 198 17 081 A1). For obtaining the ingredients, there are also frequently washing processes and additional preparation steps that influence the ingredients, for instance the addition of an elution liquid. If it is to be possible to evaluate separately the result of each individual step, the individual fractions must be collected physically separately or must be able to be removed separately. Both of these options are associated with great complexity in terms of apparatus. Thus in a method for continuous purification of nucleic acid of cells, a collection tube and an outflow tube are selectively urged, by a switching mechanism, under the outlet of a filter apparatus that can be coated with different liquid compositions or different purifying liquids (DE 694 08 461 T2). The mechanism required for moving collection tube or outflow tube is relatively complex, especially if more than two containers are to be filled. In addition, without additional complexity, for instance housing the filter segment and the collection container in a common housing, it is not possible to create a hermetic seal between the liquid and the atmosphere when the liquid enters the tube.

Multistage separation under hermetic conditions is possible using series switching of a plurality of filter modules (DE 198 17 081 A1). The disadvantage of such an apparatus is comprised in that the different fractions must be manually pipetted from the liquid and purification liquids must be manually added to respective filter modules. In addition, the multistage filter unit requires a large amount of space.

Figure 1:
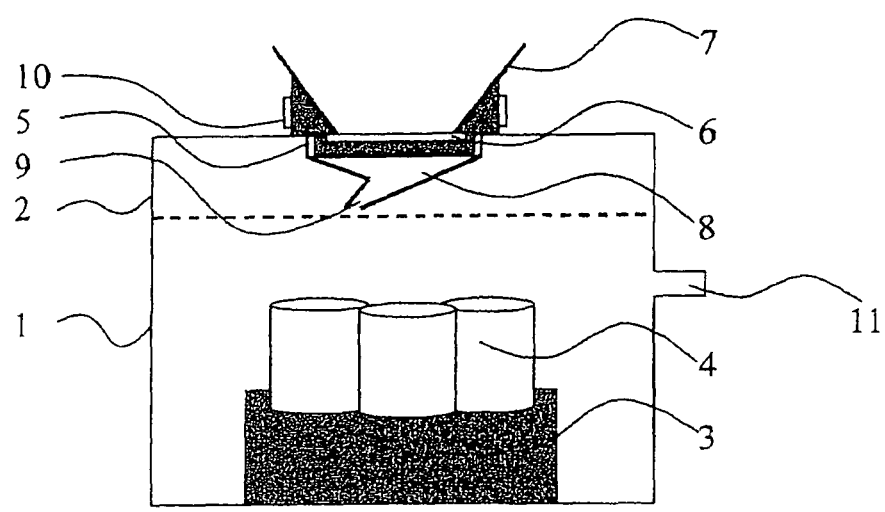
FIG. 1 shows a schematic depiction of a device for fractionation.

In the figures, particular elements of the inventive device are numbered as follows:
1. Housing
2. Cover
3. Mount
4. Test vial
5. Filter mount
6. Filter
7. Specimen feed
8. Distribution system
9. Outlet
10. Adjusting wheel
11. Adapter
12. Collection apparatus
13. Conveyor mechanism

DESCRIPTION OF THE INVENTION

In contrast, the inventive apparatus has the advantage that it is constructed very compactly. At least two containers are arranged in one housing and can be connected to a distribution system, the outlet of which can be repositioned, i.e. can be oriented selectively toward the opening of either container. The outlet of a separation apparatus opens into the distribution system. This substantially reduces the complexity of the fractionation device. In addition, the apparatus also provides for rapid fractionation, as is required in particular for biological investigations. After the separation process is complete, the distribution system switches immediately to the next container in which the liquid from the next separation process is captured, which next process may be performed in the same separation apparatus.

All apparatus that are known for separation can be used as separation apparatus in which the liquid to be fractionated can be removed from the apparatus with nothing further. Apparatus that are especially suitable are those in which the liquid leaves the apparatus due solely to its gravity and thus automatically travels into the distribution system arranged therebelow and into the collection apparatus. This occurs e.g. with filters.

It is also advantageous that in accordance with the method for fractionation of the present invention, the liquid leaving the separation apparatus can be captured in a controlled manner as a function of event or time without there having to be a discrete separation apparatus with collection apparatus for each specimen or the separation apparatus having to be moved to each collection container or the collection containers having to be positioned under the separation apparatus. The control can be controlled as a function of each separation process, which can be determined by the liquids used, for instance wash liquids, or even by time factors. Likewise, it is possible to control the fractionation downstream of the site at which the liquid is removed. The fractionation method is universally applicable because it is independent of how the liquid leaving the separation apparatus occurs, its composition, and its qualities.

All common methods can be used for separation methods, such as filtration, chromatographic methods, dialysis, gravimetric separation, separation by means of electrostatic forces, or even centrifugation.

In accordance with one advantageous embodiment of the invention, the collection apparatus comprises a hermetically sealable housing. The containers are hermetically sealed in the housing relative to the environment. This is necessary for fractionating and maintaining those liquids that require certain properties for the atmosphere surrounding them, for instance a certain degree of purity. In addition, in this way it is possible, for instance for accelerating the separation process by means of a filter, to produce in a simple manner a drop in pressure in the entire apparatus via the filter. For this it is only necessary to attach the housing to an evacuation pump.

In accordance with another advantageous embodiment of the invention, the distribution system is integrated into the collection apparatus, which has a connector for the separation apparatus on its top side. On the other hand, the distribution system can also be integrated into the separation apparatus. Both variants have the advantage that the fractionation device then comprises only two main assemblies that either form one compact unit or can even also exist as separate assemblies. The variant of the integration of the distribution system in the collection apparatus as a separate assembly has the advantage that this compact structure is easily transportable and therefore can be attached to any separation apparatus that are connected stationary. In this manner it is much easier to provide hermetic transfer of the liquid from the separation apparatus into the containers. Due to the more flexible applicability and better cleaning potential it is advantageous to connect the assemblies to one another in a detachable manner.

In accordance with another advantageous embodiment of the invention, separation apparatus, distribution system, and collection apparatus are housed in a common housing. Such a compact fractionation apparatus has the advantage that it does not require much space and is easily transportable. On its top side it has a connector for supplying the liquid to be separated and it can thus be connected to any desired sources. A positioning mechanism that can be accessed from the exterior makes it possible to operate the distribution system.

In accordance with another advantageous embodiment of the invention, the collection apparatus has a connector for connecting to a vacuum pump. This is advantageous for instance for producing a drop in pressure via a filter, in particular when the filter is integrated in the collection apparatus.

In accordance with yet another advantageous embodiment of the invention, the distribution system comprises a tube, which rotates about a vertical axis, or capillary that can be rotated from the exterior. The individual containers are arranged beneath the outlet of the tube or the capillary on the circumference of the circle that the outlet describes when the tube or capillary is rotated. Containers arranged in concentric circles about the axis of rotation of the tube can even be filled by shortening or lengthening the outlet. In accordance with still another advantageous embodiment of the invention, the distribution system has an outlet that can be displaced translationally in the horizontal plane and that is displaced to the respective container on tracks that run parallel and perpendicular to one another. The movement of the outlet of the distribution system can occur in prescribed fixed steps or in a stepless manner.

In a further embodiment of the invention that is advantageous in this regard the distribution system works by means of electromagnetic deflection of the stream of liquid.

In one additional embodiment of the invention, a plurality of autonomous units that comprise collection apparatus and distribution system and that have the same shape and size are arranged in series with one another to form a preparation system. This is necessary when a plurality of different liquids are to be fractionated. The individual fractions of each liquid are filled in the containers via the distribution system that belongs to each collection apparatus. Then the preparation system with the next collection apparatus is placed thereebeneath or beneath a subsequent separation apparatus. The preparation system can be moved translationally for this purpose.

In accordance with another advantageous embodiment of the invention, a computer program assumes the routines of filling the individual autonomous units with the liquid or liquids. This simplifies making the times for filling more flexible and adding control routines.

In the embodiment of the method for fractionating particle-containing liquids, the distribution system is controlled as a function of the fractionation process. The control can be a control that is determined by the separation process itself, for instance by different washing processes. However, it can also be a control as a function of processes upstream of the separation process. These can be certain mixing or identification processes, for instance. However, the distribution system can also be controlled as a function of the temporal and/or local origin of the liquid specimens.

Additional advantages and advantageous embodiments of the invention can be taken from the following exemplary description, the drawings, and the claims.

The present invention in one of its embodiments is now discussed in more detail with reference to the drawings. The numbers correspond to the elements of the device as noted in the figures.

Figure 2:
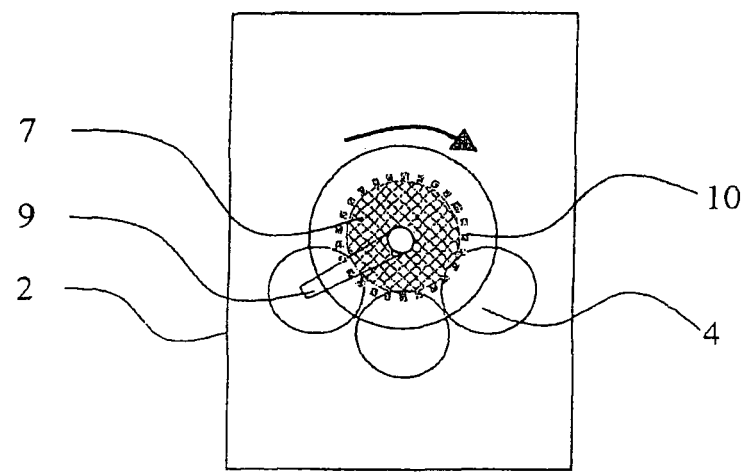
FIG. 2 is a top view of the device depicted in FIG. 1.

FIG. 1 shows a compact device for fractionation according to an embodiment of the invention in which all components are housed in the collection apparatus. The device comprises a housing 1 that can be sealed with a cover 2. Retainably housed in the housing 1 is a mount 3 that securely and fixedly receives test vials 4. Disposed in the cover 2 is an opening into which a filter mount 5 with a filter 6 is placed. A funnel-like specimen feed 7 is placed on the filter mount 5 above the cover 2. Disposed below the filter mount 5 is a distribution system 8 having an outlet 9 that is rotatably borne in the cover 2 about the axis of the filter mount 5 or the specimen feed 7 and that is joined rotation-fast above the cover 2 to an adjusting wheel 10 that surrounds the specimen feed 7. As can be seen from FIG. 2, the outlet 9 of the distribution system 8 can be moved on a horizontal circular track into any desired position, and thus to the openings of the test vials 4, using the adjusting wheel 10. An adapter 11 for connecting to a vacuum pump is disposed on the housing 1.

The use of the inventive fractionation device shall be described using examples in the following. The liquid to be fractionated is a particle suspension of cells, organs, organisms, or their constituent parts dissolved in a liquid or dissolved tissue. The particle suspension is washed in a first step. Bidistilled or deionized water, sodium solution phosphate buffer, nutrient solution, or other solutions can be used for wash solution A. The wash solution can be added to the particle suspension sequentially or simultaneously. Prior to adding the next liquid to the particle suspension the preceding process must be concluded and the distribution system 8 is switched to the next test vial 4. One test vial 4 is provided for each filtrate. After the wash process a solution B can be added that is a liquid that causes cell lysis or brings about membrane permeability. Among these are alkali or acidic solutions, solutions having biologically active components such as enzymes, phages, or perforines, liquids with high or low osmolarity or high or low temperature. Solution B can furthermore be a solution having modifying components that contain for instance trypsin, derivatising substances, staining substances, or the like.

In the following some information regarding working values for the preparation system is provided.

The volume of the particle suspensions is 0.5 to 5 mL, generally 2 mL, the volume of the wash solution is 0.5 to 5 mL, generally 2 mL. The bidistilled or deionized water is added at a starting temperature of 95° C. with a volume of 0.5 to 5 mL, generally 2 mL. The filter has a pore size of 0.2 µm. At a filtration rate of on average 0.5 to 2.0 mL/s, generally 1.0 mL/s, the filtration time between the applied cell solution and the subsequent wash step, on the one hand, and the complete filtration of the wash solution and the subsequent beginning of filtration of the cell disruption solution, on the other hand, is between 0.25 and 1.0 s, generally 0.5 s, so that between 1.0 and 32.0 s, generally 6.0 s, are needed for the entire sequence. The three filtrates are each collected in separate test vials 4. The driving force of the filtration is produced by a vacuum in the housing 1.

Figure 3:
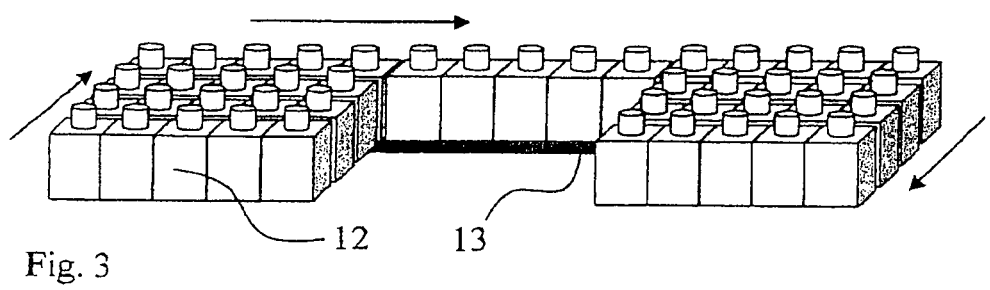
FIG. 3 shows a preparation system according to the present invention having a plurality of containers.

The arrangement of a plurality of independent units of collection apparatus 12 for a preparation system in which the collection apparatus are supplied by means of a conveyor mechanism 13 of a separation apparatus (not depicted in greater detail) and are moved away again after filling is depicted in FIG. 3. The separation apparatus is disposed in the area where the collection apparatus are separated into one row.

All of the features depicted in the specification, in the claims hereinafter, and in the drawings can be essential to the invention both individually and in any desired combination with one another.

The invention claimed is:

1. A device for fractionating particulate-containing liquids, comprising:
   a) a separation apparatus for separating particulates, comprising: a filter operable to separate particles, a feed opening, and an outlet, wherein the feed opening is in liquid communication with and receives particulate-containing liquid from the exterior of the device;
   b) a distribution apparatus in liquid communication with the outlet of the separation apparatus and having a repositionable outlet, comprising: a liquid conduit that is rotatable about a vertical axis;
   c) a collection apparatus in fluid communication with the repositionable outlet of the distribution apparatus, the collection apparatus, comprising: at least a first and second fluid containers, each container having an input opening for receiving fractionated liquid from the repositionable outlet of the distribution apparatus, wherein the fractionated liquid from the distribution apparatus can be selectively distributed to the input openings of the containers; and,
   d) a common container; wherein:
      i. the separation apparatus is received in the common container;
      ii. the distribution apparatus and the collection apparatus are enclosed within the common container; and,
      iii. the interior of the common container and the received portion of the separation apparatus are sealed to the exterior to support a vacuum as compared to the exterior.

2. The device of claim 1, wherein the common container, further comprises: a connector that is connectable to a vacuum source.

3. The device claim 1, wherein the collection apparatus, further comprises: at least a third fluid container.

4. The device of claim 1, further comprising:
   e) a positioning mechanism configured so as to be accessible from the exterior of the common container and separation apparatus to operate the distribution apparatus so as to bring the repositionable outlet of the distribution apparatus into fluid communication with the input opening of one of the containers of the collection apparatus.

5. The device of claim 4, wherein the distribution system is positionable in a stepless manner.

6. The device of claim 1, wherein the filter has a pore size of 0.2 μm.

7. The device of claim 1, wherein the feed opening of the separation apparatus is a funnel-like specimen positioned above, and in liquid communication with, the separation apparatus.

8. The device of claim 1, wherein the fluid containers have a volume of from 0.5 to 5 mL.

9. A preparation system, comprising: at least two devices for fractionating particulate-containing liquids, the devices, comprising:
   a) a separation apparatus for separating particulates, comprising: a filter operable to separate particles, a feed opening, and an outlet, wherein the feed opening is in liquid communication with and receives particulate-containing liquid from the exterior of the device;
   b) a distribution apparatus in liquid communication with the outlet of the separation apparatus and having a repositionable outlet, comprising: a liquid conduit that is rotatable about a vertical axis;
   c) a collection apparatus in fluid communication with the repositionable outlet of the distribution apparatus, the collection apparatus, comprising: at least a first and second fluid containers, each container having an input opening for receiving fractionated liquid from the repositionable outlet of the distribution apparatus, wherein the fractionated liquid from the distribution apparatus can be selectively distributed to the input openings of the containers; and,
   d) a common container; wherein:
      i. the separation apparatus is received in the common container;
      ii. the distribution apparatus and the collection apparatus are enclosed within the common container; and,
      iii. the interior of the common container and the received portion of the separation apparatus are sealed to the exterior to support a vacuum as compared to the exterior;
   wherein the devices operate autonomously.

10. The preparation system of claim 9 wherein each common container of each device, further comprises: a connector that is connectable to a vacuum source.

11. The preparation system of claim 9 wherein each collection apparatus, further comprises: at least a third fluid container.

12. The preparation system of claim 9 wherein each device, further comprises:
    e) a positioning mechanism configured so as to be accessible from the exterior of the common container and separation apparatus to operate the distribution apparatus so as to bring the repositionable outlet of the distribution apparatus into fluid communication with the input opening of one of the containers of the collection apparatus.

13. The preparation system of claim 9 wherein each distribution system is positionable in a stepless manner.

14. The preparation system of claim 9 wherein each filter has a pore size of 0.2 μm.

15. The preparation system of claim 9 wherein each feed opening of each separation apparatus is a funnel-like specimen positioned above, and in liquid communication with, the separation apparatus.

16. The preparation system of claim 9, further comprising: a conveyor mechanism capable of moving the at least two devices.

17. The preparation system of claim 16, further comprising: a program sequencer adapted to introduce particulate-containing liquid to the feed openings of the individual separation apparatus of the devices for fractionating particulate-containing liquids in a programmed sequence.

18. The preparation system of claim 9, wherein each of the fluid containers have a volume of from 0.5 to 5 mL.

19. A method of fractionating particulate-containing liquid, comprising:
   a) providing at least one device for fractionating particulate-containing liquid, the device, comprising:
      I. a separation apparatus for separating particulates, comprising: a filter operable to separate particles, a feed opening, and an outlet, wherein the feed opening is in liquid communication with and receives particulate-containing liquid from the exterior of the device;
      II. a distribution apparatus in liquid communication with the outlet of the separation apparatus and having a repositionable outlet, comprising: a liquid conduit that is rotatable about a vertical axis;
      III. a collection apparatus in fluid communication with the repositionable outlet of the distribution apparatus, the collection apparatus, comprising: at least a first and second fluid containers, each container having an input opening for receiving fractionated liquid from the repositionable outlet of the distribution apparatus, wherein the fractionated liquid from the distribution apparatus can be selectively distributed to the input openings of the containers; and,
      IV. a common container; wherein:
         i. the separation apparatus is received in the common container;
         ii. the distribution apparatus and the collection apparatus are enclosed within the common container; and,
         iii. the interior of the common container and the received portion of the separation apparatus are sealed to the exterior to support a vacuum as compared to the exterior;
   b) introducing a particle suspension of cells to the separation apparatus via the feed opening thereof;
   c) passing the resulting liquid fraction of the suspension of cells through the separation apparatus while retaining the cells of the suspension of cells in the separation apparatus;
   d) distributing the liquid fraction to the first container via the distribution apparatus;
   e) moving the outlet of the distribution apparatus into liquid communication with the second container of the collection apparatus;
   introducing a first solution to the separation apparatus via the feed opening thereof, the first solution being capable of permeabilizing or lyzing retained cells to release intracellular metabolites; and,
   g) distributing the resulting metabolite solution to the second container via the distribution apparatus.

20. The method of claim 19, further comprising:
   h) applying a vacuum in the interior of the common container and received portion of the separation apparatus as compared to the exterior, whereby the vacuum aids in drawing the liquid through the filter of the separation apparatus.

21. The method of claim 19, further comprising:
   i) selecting the manner of introducing particulate-containing liquid and further liquids and selectively moving the outlet of the distribution apparatus as a function of the principal of operation of the separation apparatus.

22. The method of claim 19, wherein:
   the device further comprising: a third liquid container;
   the method further comprising:
   j) prior to introducing the first solution, introducing a wash solution to the separation apparatus via the feed opening thereof, the wash solution being capable of washing the retained cells;
   k) passing the resulting wash fraction through the separation apparatus while retaining cells of the suspension of cells in the separation apparatus;
   l) distributing the wash fraction to the second container via the distribution apparatus; and,
   m) moving the outlet of the distribution apparatus to the third container of said collection apparatus.

23. The method of claim 22, further comprising:
   n) applying a vacuum in the interior of the common container and received portion of the separation apparatus as compared to the exterior, whereby the vacuum aids in drawing the liquid through the filter of the separation apparatus.

24. The method of claim 19, wherein the entire sequence requires less than 32 s.

25. The method of claim 19, wherein the entire sequence requires less than 6 s.

26. A method for fractionating a particle suspension of cells, comprising: providing at least one preparation system according to claim 9, wherein:
   a) the autonomous devices are sequentially fed from a continuous flow of a particle suspension of cells; and,
   b) each autonomous device subsequently fractionates the received particle suspension of cells.

* * * * *